United States Patent
Shaw et al.

(10) Patent No.: US 11,545,267 B2
(45) Date of Patent: Jan. 3, 2023

(54) METHODS AND APPARATUS FOR THE APPLICATION OF REINFORCEMENT LEARNING TO ANIMAL MEDICAL DIAGNOSTICS

(71) Applicant: SignalPET, LLC, San Diego, CA (US)

(72) Inventors: Neil Gavin Shaw, San Diego, CA (US); Lior Kuyer, San Diego, CA (US)

(73) Assignee: SIGNALPET, LLC, San Diego, CA (US)

( * ) Notice: Subject to any disclaimer, the term of this patent is extended or adjusted under 35 U.S.C. 154(b) by 0 days.

(21) Appl. No.: 16/985,106

(22) Filed: Aug. 4, 2020

(65) Prior Publication Data

US 2022/0044815 A1 Feb. 10, 2022

(51) Int. Cl.
*G16H 50/30* (2018.01)
*G06N 20/00* (2019.01)
*G16H 10/40* (2018.01)
*G06K 9/62* (2022.01)

(52) U.S. Cl.
CPC .......... *G16H 50/30* (2018.01); *G06K 9/6267* (2013.01); *G06N 20/00* (2019.01); *G16H 10/40* (2018.01)

(58) Field of Classification Search
CPC ........ G16H 50/30; G16H 10/40; G06N 20/00; G06K 9/6267
See application file for complete search history.

(56) References Cited

U.S. PATENT DOCUMENTS

| | | |
|---|---|---|
| 9,569,736 B1 | 2/2017 | Ghesu et al. |
| 9,940,711 B2 | 4/2018 | Bregman-Amitai |
| 10,039,513 B2 | 8/2018 | Bregman-Amitai |
| 10,111,637 B2 | 10/2018 | Bregman-Amitai |
| 10,593,041 B1 | 3/2020 | Shaw |

(Continued)

FOREIGN PATENT DOCUMENTS

| | | |
|---|---|---|
| KR | 101884609 | 8/2018 |
| WO | WO2018119766 | 7/2018 |
| WO | 2019179857 | 9/2019 |

OTHER PUBLICATIONS

La Perle KMD. Machine Learning and Veterinary Pathology: Be Not Afraid! Vet Pathol. Jul. 2019;56(4):506-507. doi: 10.1177/0300985819848504. PMID: 31185880. (Year: 2019).*

*Primary Examiner* — Michael Tomaszewski
*Assistant Examiner* — Mohmad Muqueeth
(74) *Attorney, Agent, or Firm* — Garson & Gutierrez, PC

(57) ABSTRACT

Methods and apparatus for the application of reinforcement learning to animal medical diagnostics. In one embodiment, a system is disclosed that utilizes two (2) RL agents that are arranged sequentially and that are optimized independently from one another. The first RL agent is an assessment RL agent which takes as input from one or more of: outputs from classification artificial intelligence (AI) engines; outputs from subjective biological data storage devices, and outputs from objective biological data storage devices. Using these input(s), the assessment RL agent outputs a set of assessments which evaluate a set of conditions associated with an animal. This set of assessments is then provided as input to a second RL agent known-as a plan RL agent which determines a set of treatment recommendations and diagnostics based off this determined set of assessments. Methods and computer-readable media are also disclosed.

16 Claims, 12 Drawing Sheets

(56) References Cited

U.S. PATENT DOCUMENTS

| | | |
|---|---|---|
| 2008/0214907 A1 | 9/2008 | Gutkowicz-Krusin et al. |
| 2010/0070293 A1 | 3/2010 | Brown et al. |
| 2011/0216180 A1 | 9/2011 | Pasini |
| 2012/0183188 A1 | 7/2012 | Moriya |
| 2013/0004043 A1 | 1/2013 | Ross et al. |
| 2013/0070986 A1 | 3/2013 | Peleg et al. |
| 2013/0268203 A1 | 10/2013 | Pyloth |
| 2015/0363564 A1* | 12/2015 | Lai ............... G06F 19/3418 705/2 |
| 2018/0096477 A1 | 4/2018 | Avila |
| 2018/0192944 A1 | 7/2018 | Diener et al. |
| 2018/0242943 A1 | 8/2018 | Bregman-Amitai et al. |
| 2019/0005684 A1* | 1/2019 | De Fauw ............ G06K 9/6262 |
| 2019/0046146 A1 | 2/2019 | Bregman-Amitai et al. |
| 2019/0340753 A1 | 11/2019 | Brestel et al. |
| 2020/0226748 A1 | 7/2020 | Kaufman et al. |

\* cited by examiner

METHODS AND APPARATUS FOR THE APPLICATION OF REINFORCEMENT LEARNING TO ANIMAL MEDICAL DIAGNOSTICS

RELATED APPLICATIONS

This application is related to U.S. patent application Ser. No. 16/783,578 filed Feb. 6, 2020 and entitled "Methods and Apparatus for the Application of Machine Learning to Radiographic Images of Animals", which is a divisional of and claims the benefit of priority to U.S. patent application Ser. No. 16/578,182 filed Sep. 20, 2019 and entitled "Methods and Apparatus for the Application of Machine Learning to Radiographic Images of Animals", now U.S. Pat. No. 10,593,041, which claims the benefit of priority to U.S. Provisional Patent Application Ser. No. 62/808,604 filed Feb. 21, 2019 and entitled "Methods and Apparatus for the Application of Machine Learning to Radiographic Images of Animals", the contents of each of the foregoing being incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE DISCLOSURE

1. Technological Field

The present disclosure relates generally to the application of machine learning to subjective and objective biological data received from living beings, and more particularly in one exemplary aspect to the application of reinforcement learning methodologies to subjective and objective biological data of various animal species including, inter alia, canines, felines, other domesticated and non-domesticated animals, and humans.

2. Field of the Disclosure

The utilization of machine learning, and in particular supervised and unsupervised learning as well as reinforcement learning (RL), is a relatively nascent technology as applied to various software services and applications. For example, RL is an area of machine learning that utilizes so-called software agents that take actions in an environment in order to maximize the notion of cumulative reward. In other words, RL can not only maximize immediate rewards resultant from immediate actions, RL can also maximize long term rewards while taking a series of actions with less immediate reward impact through the application of the concept known as discounted rewards. While the application of RL has been used successfully in a variety of scenarios such as urban traffic control, control of remotely controlled drones, as well as navigating through various video game environments, there are nearly a limitless number of applications of RL that have yet to be envisioned. Accordingly, despite the widespread success of RL applications in a variety of operating scenarios, it would be desirable to apply the benefits of RL to other fields of use; particularly fields of use where human resources are limited and outcomes are time-sensitive such as in, for example, veterinary as well as human medicine.

SUMMARY

The present disclosure satisfies the foregoing needs by providing, inter alia, methods and apparatus for the application of RL to animal medical diagnostics.

In one aspect, a method for the application of reinforcement learning (RL) to the treatment of animals is disclosed. In one embodiment, the method includes determining a set of assessments, using an assessment RL agent, based on a set of observations; determining a set of plans based on the determined set of assessments using a plan RL agent; storing the determined set of assessments and the determined set of plans in a historical log storage device; and receiving feedback on the determined set of assessments and the determined set of plans.

In one variant the determined set of plans includes one or more additional set of diagnostic tests to be performed and the method further includes receiving results from the one or more additional set of diagnostic tests; inputting the results from the one or more additional set of diagnostic tests into the assessment RL agent; determining an updated set of assessments using the assessment RL agent based on the results from the one or more additional set of diagnostic tests; and generating an updated set of plans based on the determined updated set of assessments.

In another variant, when the received feedback on the determined set of assessments or the determined set of plans is negative, removing the respective stored set of assessments or the stored set of plans from the historical log storage device.

In yet another variant, the method further includes using contents of the historical log storage device to update a policy or a reward value function for either or both of the assessment RL agent and the plan RL agent.

In yet another variant, the method further includes receiving one or more of outputs from: one or more classification artificial intelligence engines, an objective biological data storage device, and a subjective biological data storage device, in order to determine the set of observations.

In yet another variant, the method further includes using one or more human-based assessments as input to the plan RL agent to determine the set of plans using the plan RL agent.

In yet another variant, the method further includes updating a policy or a reward state value function for the assessment RL agent independently from an updating of a policy or a reward state value function for the plan RL agent.

In another aspect, a non-transitory computer-readable storage apparatus is disclosed. In one embodiment, the non-transitory computer-readable storage apparatus includes a plurality of instructions, that when executed by a processor apparatus, are configured to: receive a set of observations related to treatment of an animal; determine a set of assessments, using an assessment reinforcement learning (RL) agent, based on the received set of observations; determine a set of plans based on the determined set of assessments using a plan reinforcement learning (RL) agent; store the determined set of assessments and the determined set of plans in a historical log storage device; and receive feedback on the determined set of assessments and the determined set of plans.

In one variant, the plurality of instructions, that when executed by the processor apparatus, are further configured to: output one or more additional set of diagnostic tests to be performed as part of the determined set of plans; receive results from the one or more additional set of diagnostic tests; input the results from the one or more additional set of diagnostic tests into the assessment RL agent; determine an updated set of assessments using the assessment RL agent based on the results from the one or more additional set of diagnostic tests; and generate an updated set of plans based on the determined updated set of assessments.

In another variant, the plurality of instructions, that when executed by the processor apparatus, are further configured to: receive feedback on the determined set of assessments or the determined set of plans that is negative; and remove the respective stored set of assessments or the stored set of plans from the historical log storage device.

In yet another variant, the plurality of instructions, that when executed by the processor apparatus, are further configured to: use contents of the historical log storage device in order to update a policy or a reward value function for either or both of the assessment RL agent and the plan RL agent.

In yet another variant, the received set of observations related to the treatment of the animal includes receipt of one or more outputs from: one or more classification artificial intelligence engines, an objective biological data storage device, and a subjective biological data storage device.

In yet another variant, the plurality of instructions, that when executed by the processor apparatus, are further configured to: use one or more human-based assessments as input to the plan RL agent to determine the set of plans using the plan RL agent.

In yet another variant, the plurality of instructions, that when executed by the processor apparatus, are further configured to: update a policy or a reward state value function for the assessment RL agent independently from an update of a policy or a reward state value function for the plan RL agent.

In yet another aspect, a system configured to apply reinforcement learning (RL) to the treatment of animals is disclosed. In one embodiment, the system includes: a classification artificial engine that takes as input radiographic images, and outputs classifications for various conditions of an animal; a subjective biological data storage device that stores subjective biological data for the animal; an objective biological data storage device that stores objective biological data for the animal; an assessment RL agent which takes as input the classifications for the various conditions of the animal from the classification artificial engine, the subjective biological data for the animal from the subjective biological data storage device, and the objective biological data for the animal from the objective biological data storage device, and outputs a determined set of assessments for the animal based on the inputs; a plan RL agent which takes as input the determined set of assessments for the animal from the assessment RL agent, and outputs a determined set of plans for the treatment of the animal based on the set of assessments from the assessment RL agent; and a historical log storage device which stores the determined set of assessments and the determined set of plans.

In one variant, the determined set of plans includes one or more additional set of diagnostic tests to be performed; the assessment RL agent receives as input results from the one or more additional set of diagnostic tests in order to generate an updated set of assessments; and the plan RL agent receives as input the updated set of assessments and in response thereto, generates an updated set of plans for the treatment of the animal.

In another variant, contents within the historical log storage device are utilized to update a policy or a reward value function for either or both of the assessment RL agent and the plan RL agent.

In yet another variant, the policy or the reward value function for the assessment RL agent is updated independently from the policy or the reward value function for the plan RL agent.

In yet another variant, the plan RL agent further takes as input one or more human-based assessments, the one or more human-based assessments and the determined set of assessments from the assessment RL agent being utilized for the determined set of plans generated by the plan RL agent.

In yet another variant, a portion of the contents of the historical log storage device is selectively removed based the update to the reward value function for either or both of the assessment RL agent and the plan RL agent.

In yet another aspect, an assessment reinforcement learning (RL) agent is disclosed.

In yet another aspect, a plan reinforcement learning (RL) agent is disclosed.

Other features and advantages of the present disclosure will immediately be recognized by persons of ordinary skill in the art with reference to the attached drawings and detailed description of exemplary implementations as given below.

BRIEF DESCRIPTION OF THE DRAWINGS

The features, objectives, and advantages of the present disclosure will become more apparent from the detailed description set forth below when taken in conjunction with the drawings, wherein:

FIG. 5D is a fourth exemplary graphical user interface display indicative of an assessment for a given animal, in accordance with the principles of the present disclosure.

FIG. 6C is a seventh exemplary graphical user interface display indicative of a set of assessment findings for a given animal, when one of the tests has been negated, in accordance with the principles of the present disclosure.

Figure 1:
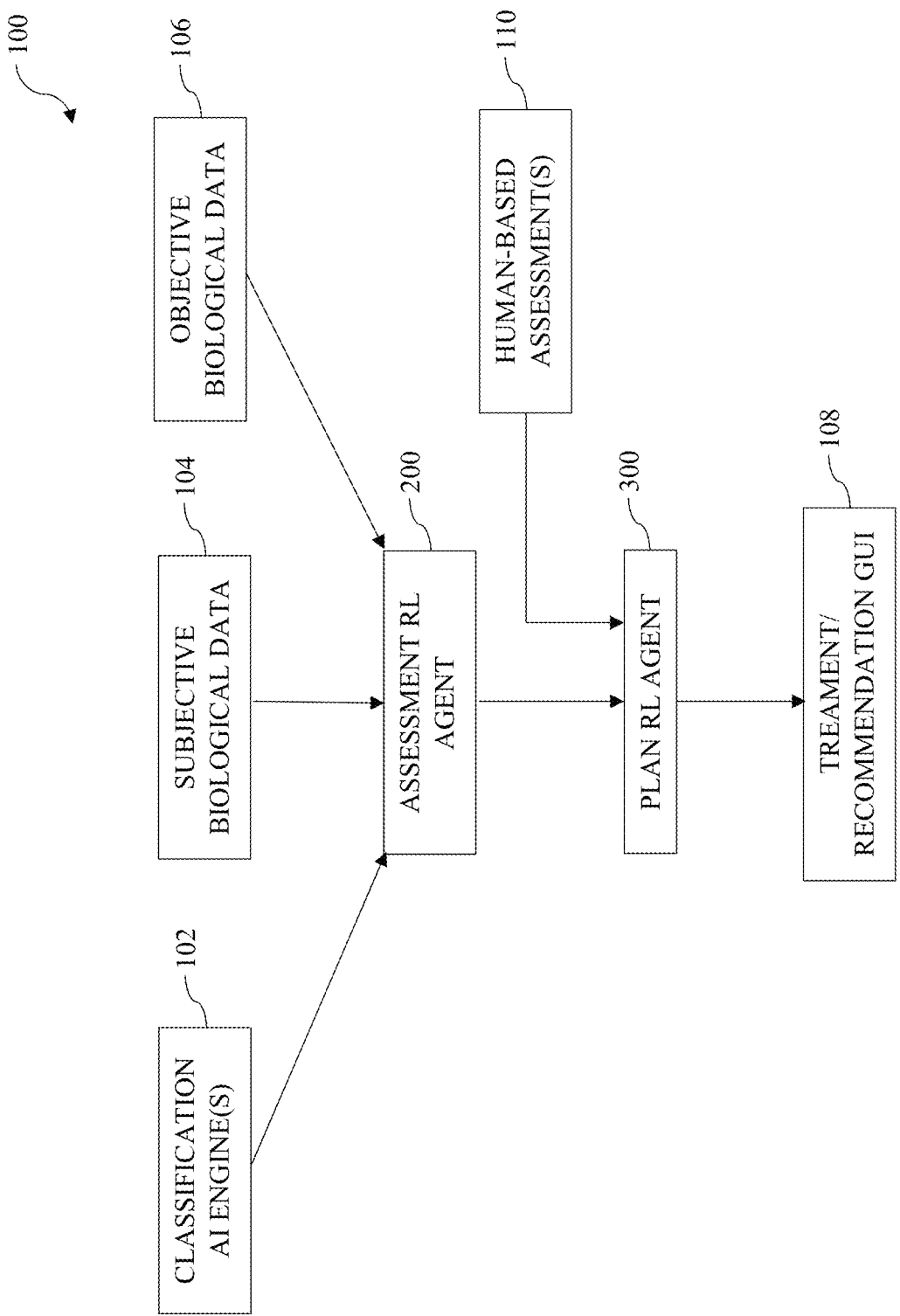
FIG. 1 is a logical block diagram of one exemplary system for providing treatments and/or recommendations using subjective and objective biological data, in accordance with the principles of the present disclosure.

All Figures disclosed herein are © Copyright 2020 SignalPET, LLC. All rights reserved.

DETAILED DESCRIPTION

Overview

The present disclosure provides for systems, apparatus, computer-readable media, and methods for the application of RL to the treatment and recommendation of diagnostics for, inter alia, veterinary medicine. In one embodiment, a system is disclosed that utilizes two (2) RL agents that are arranged sequentially and that are optimized independently from one another. The first RL agent is an assessment RL agent which takes as input from one or more of: outputs from classification artificial intelligence (AI) engines as-is described in commonly owned U.S. patent application Ser. No. 16/578,182 filed Sep. 20, 2019 and entitled "Methods and Apparatus for the Application of Machine Learning to Radiographic Images of Animals", now U.S. Pat. No. 10,593,041, the contents of which were previously incorporated herein by reference supra; outputs from subjective biological data storage devices, and outputs from objective biological data storage devices. Using these input(s), the assessment RL agent outputs a set of assessments which evaluate a set of conditions associated with an animal. This set of assessments is determined based on an established policy for the assessment RL agent which utilizes a reward value function that takes into consideration short term and/or long-term rewards for its operation.

This set of assessments is then provided as input to a second RL agent known-as a plan RL agent. The plan RL agent is operated and optimized independently from the assessment RL agent and utilizes its own policy and reward value function that takes into consideration short term and/or long term rewards in order to generate a set of treatment and diagnostic recommendations based on the received set of assessments. In some implementations, the plan RL agent may take into consideration human-based assessments in addition to, or alternatively from, the set of assessments generated by the assessment RL agent. In instances in which the plan RL agent generates one or more additional diagnostic tests to be performed, the sequence of RL agents may be recursively run to generate optimized treatment recommendation for the animal. Specific implementation examples for the system are also disclosed herein.

Exemplary Embodiments

Detailed descriptions of the various embodiments and variants of the apparatus and methods of the present disclosure are now provided. It is noted that wherever practicable similar or like reference numbers may be used in the figures and may indicate similar or like functionality. The figures depict embodiments of the disclosed system, reinforcement learning agent(s), methods, or graphical user interfaces (GUIs) for purposes of illustration only. One skilled in the art will readily recognize from the following description that alternative embodiments of the structures and methods illustrated herein may be employed without necessarily departing from the principles described herein.

Additionally, while systems are discussed in the context of the application of reinforcement learning agents in the context of the machine learning principles discussed in co-owned U.S. patent application Ser. No. 16/578,182 filed Sep. 20, 2019 and entitled "Methods and Apparatus for the Application of Machine Learning to Radiographic Images of Animals", now U.S. Pat. No. 10,593,041, the contents of which were previously incorporated herein by reference supra, it would be readily appreciated that the structures and methods described herein may be practiced independent from the aforementioned machine learning principles described therein. Moreover, while the use of subjective biological data and objective biological data is considered exemplary, it would be recognized that the principles described herein may be applied to either subjective biological data or objective biological data in some implementations.

Moreover, while exemplary embodiments are described in the context of an exemplary system that includes a single assessment RL agent and/or a single plan RL agent, it would be readily appreciated that embodiments discussed herein may include more than one assessment RL agent and/or more than one plan RL agent in some embodiments. For example, the principles described herein may employ so-called "ensemble methods", where two or more assessment RL agents and/or two or more plan RL agents may be employed to produce a more optimal predictive model (e.g., democratized determinations). While not expressly described in detail herein, the application of ensemble methodologies to the exemplary assessment RL agents and plan RL agents described herein would be readily apparent to one of ordinary skill given the contents of the present disclosure.

Exemplary Treatment/Diagnostic System(s)—

Referring now to FIG. 1, one exemplary system 100 for providing treatment and/or diagnostic recommendations of an animal (e.g., canines, felines, humans, etc.) based on biological data are shown and described in detail. The functionality of the various modules described herein may be implemented through the use of software executed by one or more processors (or controllers) and/or may be executed via the use of one or more dedicated hardware modules, with the architecture of the system being specifically optimized to execute the artificial intelligence and/or machine learning architectures discussed herein. The computer code (software) disclosed herein is intended to be executed by a computing system that is able to read instructions from a non-transitory computer-readable medium and execute them in one or more processors (or controllers), whether off-the-shelf or custom manufactured. The computing system may be used to execute instructions (e.g., program code or software) for causing the computing system to execute the computer code described herein. In some implementations, the computing system operates as a standalone device or a connected (e.g., networked) device that connects to other computer systems. The computing system may include, for example, a personal computer (PC), a tablet PC, a notebook computer, or other custom device capable of executing instructions (sequential or otherwise) that specify actions to be taken. In some implementations, the computing system may include a server. In a networked deployment, the computing system may operate in the capacity of a server or client in a server-client network environment, or as a peer device in a peer-to-peer (or distributed) network environment. Moreover, a plurality of computing systems may operate to jointly execute instructions to perform any one or more of the methodologies discussed herein.

An exemplary computing system includes one or more processing units (generally processor apparatus). The processor apparatus may include, for example, a central processing unit (CPU), a graphics processing unit (GPU), a digital signal processor (DSP), a controller, a state machine, one or more application specific integrated circuits (ASICs), one or more radio-frequency integrated circuits (RFICs), or any combination of the foregoing. The computing system also includes a main memory. The computing system may include a storage unit. The processor, memory and the storage unit may communicate via a bus.

In addition, the computing system may include a static memory, a display driver (e.g., to drive a plasma display panel (PDP), a liquid crystal display (LCD), a projector, or other types of displays). The computing system may also include input/output devices, e.g., an alphanumeric input device (e.g., touch screen-based keypad or an external input device such as a keyboard), a dimensional (e.g., 2-D or 3-D) control device (e.g., a touch screen or external input device such as a mouse, a trackball, a joystick, a motion sensor, or other pointing instrument), a signal capture/generation device (e.g., a speaker, camera, and/or microphone), and a network interface device, which may also be configured to communicate via the bus.

Embodiments of the computing system corresponding to a client device may include a different configuration than an embodiment of the computing system corresponding to a server. For example, an embodiment corresponding to a server may include a larger storage unit, more memory, and a faster processor but may lack the display driver, input device, and dimensional control device. An embodiment corresponding to a client device (e.g., a personal computer (PC)) may include a smaller storage unit, less memory, and a more power efficient (and slower) processor than its server counterpart(s).

The storage unit includes a non-transitory computer-readable medium on which is stored instructions (e.g., software) embodying any one or more of the methodologies or functions described herein. The instructions may also reside, completely or at least partially, within the main memory or within the processor (e.g., within a processor's cache memory) during execution thereof by the computing system, the main memory and the processor also constituting non-transitory computer-readable media. The instructions may be transmitted or received over a network via the network interface device.

While non-transitory computer-readable medium is shown in an example embodiment to be a single medium, the term "non-transitory computer-readable medium" should be taken to include a single medium or multiple media (e.g., a centralized or distributed database, or associated caches and servers) able to store the instructions. The term "non-transitory computer-readable medium" shall also be taken to include any medium that is capable of storing instructions for execution by the computing system and that cause the computing system to perform, for example, one or more of the methodologies disclosed herein.

Portions of the system 100 of FIG. 1 may be located proximate to one another, while other portions may be located remote from some of the portions. For example, the subjective biological data storage device 104, the objective biological data storage device 106, and the graphical user interface (GUI) 108 may be located in, for example, the premises of the office for the treating DVM or physician, while the classification artificial intelligence(s) 102, the assessment RL agent 200, and plan RL agent 300, may be located remote from the office of the DVM or physician (e.g., within the "cloud"). Moreover, the treatment/recommendation GUI 108 may be resident in the office of, for example, the DVM or physician as well as in the office of, for example, the assignee of the present disclosure. These and other variants would be readily apparent to one of ordinary skill given the contents of the present disclosure.

In some implementations, the DVM or physician will install an application on an exemplary computing system located within, for example, the DVM's or physician's place of business. This exemplary computing system may access a remote computing system (e.g., a computing system resident in the cloud) that implements some or all of the exemplary functionality disclosed herein. For example, the DVM may capture radiographic images of a subject animal, obtain subjective and objective biological data for the subject animal, and store this data on a local computer. This data may be transmitted over a network (e.g., the Internet) to a remote computing system (e.g., resident within the cloud). This data may also contain metadata that indicates basic criteria such as, for example, (a) species; (b) breed; (c) body positioning; (d) image type; (e) testing parameters, etc., and computer code located on the remote computing system may employ machine-learning algorithms (such as those described herein), in order to verify and/or utilize such basic criteria.

The system 100 of FIG. 1 may utilize a variety of inputs as environmental observations to be utilized by the assessment RL agent 200. For example, the system 100 may utilize the outputs from one or more classification AI engines 102 as is described in commonly owned U.S. patent application Ser. No. 16/578,182 filed Sep. 20, 2019 and entitled "Methods and Apparatus for the Application of Machine Learning to Radiographic Images of Animals", now U.S. Pat. No. 10,593,041, the contents of which were previously incorporated herein by reference supra. The classification AI engines 102 may indicate the classification of a variety of differing conditions. In the context of imaging data, the classification AI engines 102 may indicate, for example, the presence (or lack of presence) of pulmonary edema, pulmonary mass(es), pleural effusion, pneumothorax, hip dysplasia, spondylosis, stifle effusion, urinary bladder calculi, as well as other types of conditions that can be assessed based on the capture of imaging data.

In some implementations, the classification AI engines 102 may indicate classifications that are broken down between: (i) thorax panels; (ii) abdomen panels; and (iii) skeleton panels. For example, a thorax panel may be further subdivided between a cardiac panel (e.g., vertebral heart score), an extrapulmonary panel (e.g., esophageal distention, esophageal foreign body, plural gas, pleural fluid), and a pulmonary panel (e.g., cranioventral, caudodorsal, and/or diffuse parenchymal patterns, patchy, bronchointerstitial and/or bronchial patterns, pulmonary mass(es), nodular or miliary patterns, or pulmonary nodul(es)). The abdomen panel may be further subdivided between a gastrointestinal panel (e.g., gastric distension, foreign material, and/or dilation and volvulus, small intestinal foreign material(s) and/or plication, populations of the small intestine and/or colonic foreign material(s)), extragastrointestinal panels (e.g., hepatomegaly, mid abdominal mass, splenomegaly, peritoneal and/or retroperitoneal fluid, and/or retroperitoneal lymphadenopathy), and a urogenital panel (e.g., renal mineralization, renomegaly, small kidney, urinary bladder calculi, urethral calculi, prostatomegaly, and/or prostatic mineralization). The skeleton panel may be further subdivided between skull and spine panels (e.g., cervical disc space narrowing, spondylosis, and/or thoracolumbar disc space narrowing), forelimb panel (e.g., appendicular fracture, aggressive bone lesion, shoulder arthropathy, flattened humeral head, and/or third phalanx bone loss), pelvis panel (e.g., pelvic fracture(s) and/or hip incongruity), and hindlimb panel (e.g., appendicular fracture, aggressive bone lesion, stifle effusion, and/or third phalanx bone loss).

This imaging data may take the form of digital imaging and communications in medicine (DICOM) images, or other two-dimensional radiographic images, as well as three-dimensional imaging data that may be received from other types of imaging apparatus, including for example, imaging data obtained from computed tomography (CT), magnetic resonance imaging (MRI), positron emission tomography (PET), single-photon emission computed tomography (SPECT), ultrasound (sonography) and/or other biological imaging techniques. The output of the classification AI engines 102 may also indicate whether or not the classifications therefrom is determined to be normal or abnormal for each of the differing conditions and may also indicate a confidence level (e.g., confident condition is normal or confident that the condition is abnormal or that the condition is likely normal or likely abnormal, etc.).

The system 100 of FIG. 1 may also utilize subjective biological data 104 for a given animal. This subjective biological data 104 may include subjective observations that are otherwise difficult to quantify or measure. For example, in the context of humans, this subjective information may include observations that are verbally expressed by the patient such as when the symptoms first started; if pain is present, the location where the pain is present, the character of the pain (e.g., stabbing, dull or aching), or if the source of the pain radiates elsewhere in the patient's anatomy; the duration of the symptom or pain; whether there may be other alleviating factors such as if there are steps being taken to mitigate symptoms or reduce the pain that is being experienced; as well as temporal patterns associated with the pain or symptoms (e.g., whether the pain or symptoms are expressed in the mornings, evenings, in the middle of the night, etc.).

For non-human animals that are unable to verbalize their observations, the owners, or caregivers (e.g., veterinarians) for these animals must be relied upon to observe this subjective biological data. For example, the owner of an animal may observe that the animal has been unusually lethargic; has been vomiting; coughing; has unusually bad breath; is chewing or licking at its skin; has diarrhea or other issues with defecation; dragging its bottom; drooling; dizziness or difficulty maintaining balance; changes in the way the animal eats; reverse sneezing; seizures or trembling; excessive thirst; and other types of subjective symptoms or behaviors.

The system 100 of FIG. 1 may also utilize objective biological data 106 such as the results from bloodwork performed or the results of cytology testing (or the cytology panels themselves). For example, in the context of bloodwork, evaluations can be performed for complete blood count (CBC) and chemical panels. CBC testing will check the total number of red blood cells as well as the hemoglobin levels within the patient's blood. The red blood cell count and hemoglobin levels may be indicative that the animal is anemic (low red blood cell count and hemoglobin levels) or polycythemic (high red blood cell count) that may be indicative of dehydration and/or other disorders. This bloodwork may also be correlated with other disorders of the patient such as abnormalities with the animal's bone marrow, spleen, or kidneys. This bloodwork may also assist with the identification of autoimmune diseases, blood cancers, kidney diseases, tick-borne or parasitic diseases, bacterial or viral infections, and other common diseases or disorders that may be correlated with the results of bloodwork. The system 100 may also include cytology samples taken of the patient that can classify reactions as, for example, inflammatory, hyperplastic, or neoplastic. The system 100 may also include historical data which can be any input, whether subjective or objective, that has occurred in the past. The system 100 may also take into consideration historical medicines taken by the patient presently or in the past. The objective biological data 106 storage device may also include vital signs such as pulse, temperature, respiratory rate for the animal as well as other types of biological data such as, for example, audio signals obtained via, for example, a stethoscope (e.g., auscultation of heart sound) and/or storage of fecal and/or other bodily fluid test results.

In some implementations, using one or more of the classification AI engine(s) 102 results, subjective biological data 104, and/or objective biological data 106, an assessment RL agent 200 may be activated. The assessment RL agent 200 may fully observe the state of all subjectives and objectives that have been triggered (e.g., "switched on") and activate zero or more assessments as output. For example, if there are N possible assessments in the world for a given animal, for any given input vector (e.g., outputs from the classification AI engine(s) 102, subjective biological data 104, and/or objective biological data 106), the assessment RL agent may choose to output zero to N assessments. As illustrated in FIG. 1, the output of a classification AI engine 102 for a given patient may trigger a first assessment as well as a second assessment. The subjective biological data 104 for the given patient may trigger the second assessment as well as a third assessment. The objective biological data 106 for the given patient may trigger the first assessment, the second assessment as well as the third assessment. While the specific example described above is arbitrary, it would be appreciated by one of ordinary skill given the contents of the present disclosure that real-world scenarios may be (and often will be) much more complex than the illustrative example discussed above.

For example, the classification AI engines 102 may indicate a vertebral heart score abnormality as well as additional abnormalities such as pulmonary mass(es) and the presence of an enlarged liver (i.e., hepatomegaly) for a given patient. Each one of these indications are part of the input vector representing the current state of the world for the assessment RL agent 200. Additionally, subjective biological data 104 may indicate lethargy, vomiting, as well as coughing for the given patient with each of these indications separately and may also be part of the input vector representing the current state of the world for the assessment RL agent 200. Finally, objective biological data 106 such as cytology samples and bloodwork may separately may also be part of the input vector representing the current state of the world for the assessment RL agent 200. As but one non-limiting example, the presence of both pulmonary mass(es) from the classification AI engine(s) 102 as well as the cytology samples from the objective biological data 106 may become part of the input vector representing the current state of the world for the assessment RL agent 200.

As will be described in additional detail with regards to FIG. 2 discussed infra, the assessment RL agent 200 will take so-called action(s) in response to observations the assessment RL agent 200 receives from one or more of the classification AI engine(s) 102, subjective biological data 104, and/or objective biological data 106. For example, an assessment RL agent 200 may receive observations from the classification AI engine(s) 102 of the presence of an enlarged liver (i.e., hepatomegaly). Based on this observation, as well as other observations from objective and/or subjective biological data, the assessment RL agent 200 may take actions such as, for example, assessing the animal with hepatitis, hepatic (liver) lipidosis, hepatotoxicity, hepatic (liver) nodular hyperplasia, neoplasm—hepatic, hyperadrenocorticism, hepatic venous congestion, and/or diabetes mellitus. For example, the observation of an enlarged liver by the classification AI engine(s) 102 in combination with a historical usage of non-steroidal anti-inflammatory drugs may result in the assessment RL agent 200 assessing these observations as hepatotoxicity. As but another non-limiting example, the observation of an enlarged liver by the classification AI engine(s) 102 in combination with objective biological data 106 (e.g., high blood sugar levels) as well as subjective biological data 104 (e.g., frequent urination and increased thirst) may result in the assessment RL agent 200 assessing these observations as diabetes mellitus. These and other assessments made by the assessment RL agent 200 would be readily apparent to one of ordinary skill given the contents of the present disclosure.

As will be described in additional detail with regards to FIG. 3 discussed infra, the plan RL agent 300 may take action(s) based on the assessment(s) received from the assessment RL agent 200. In other words, the plan RL agent 300 may take diagnostic actions (e.g., recommendation of additional diagnostic tests to further confirm a given assessment received from the assessment RL agent 200) and/or treatment actions in order to assist with the assessment abnormality identified by the assessment RL agent 200. For example, the assessment of diabetes mellitus by the assessment RL agent 200 may result in the plan RL agent 300 recommendation of further bloodwork in order to confirm this assessment and/or treatment medication(s) such as antidiabetic medication(s), weight loss recommendations, and dietary recommendations. In some implementations, the plan RL agent 300 may take into consideration human-based assessment(s) 110 in addition to, or alternatively than, the outputs from the assessment RL agent 200. As the name implies, human-based assessments 110 are assessments made by, for example, the treating doctor of veterinary medicine (DVM) in response to the treating DVM making subjective and/or objective observations. These and other treatments and/or recommendations made by the plan RL agent 300 would be readily apparent to one of ordinary skill given the contents of the present disclosure. These treatments and/or recommendations may be then provided to, for example, a client computing device where they are displayed on a treatment/recommendation GUI 108.

Herein lies one salient advantage with the principles of the present disclosure. Namely the ability for the system 100 to quickly and accurately provide treatment recommendations that may be adopted (or discarded) by, for example, the DVM; and also to provide recommendations for additional diagnostic testing that should be provided in order to further confirm (or to disaffirm) initial assessments provided by the assessment RL agent 200. For example, a given DVM may typically assess a given subset of all possible assessments based on the treating DVM's geographical location along with the types of species the treating DVM typically works with. In such a scenario, the treating DVM would be provided with a tool (e.g., the system 100 of FIG. 1) that enables the treating DVM to work through relatively uncommon assessments that the treating DVM otherwise has limited experience with. In addition to aiding the treating DVM with uncommon diseases and/or disorders, the system 100 of FIG. 1 also provides a dispassionate and objective treatment and/or diagnostic recommendation that may be overlooked by the treating DVM as the treating DVM may, for example, apply internal biases that may be affected by, for example, the subjective symptoms being provided to the treating DVM by the owner of the animal.

Exemplary Reinforcement Learning Agents—

Figure 2:
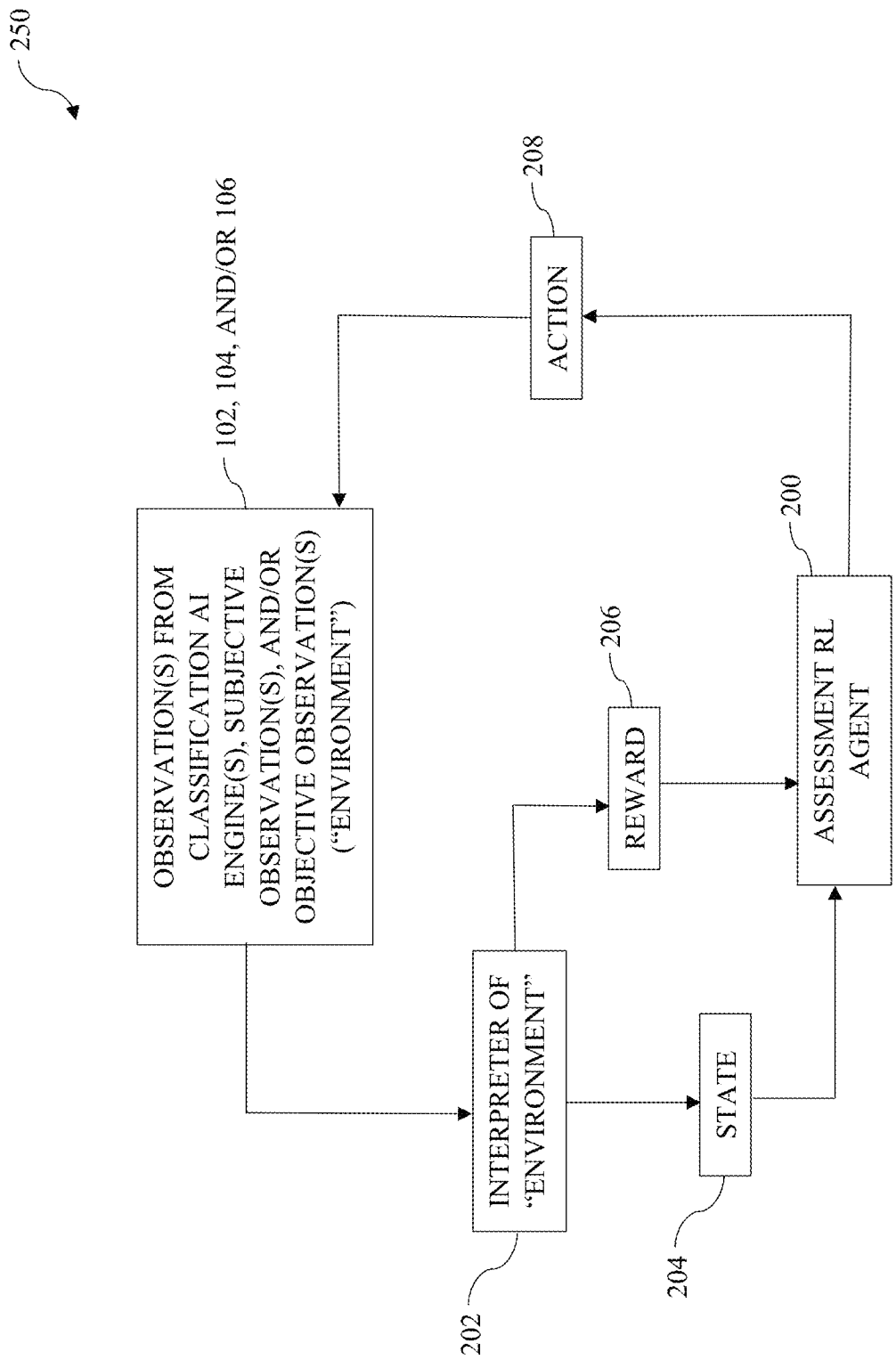
FIG. 2 is a logical block diagram of one exemplary assessment reinforcement learning agent, in accordance with the principles of the present disclosure.

Referring now to FIG. 2, an exemplary system 250 implementation of an assessment RL agent 200 is shown and described in detail. As previously discussed, RL is an area of machine learning that utilizes software agents that take actions in an environment in order to maximize the notion of cumulative reward. In other words, RL can not only maximize immediate rewards resultant from immediate actions, RL can also maximize long term rewards while taking a series of actions with less immediate reward impact through the application of the concept known as discounted rewards. The assessment RL agent's 200 environment is the set of all observations from the classification AI engine(s) 102, subjective observation(s) included in the subjective biological data store 104, as well as objective observation(s) included in the objective biological data store 106. The goal of the assessment RL agent 200 is to take the best action 208 (e.g., to provide the most correct set of diagnoses) based on the environment 102, 104, 106 that the assessment RL agent 200 observes.

The assessment RL agent 200 utilizes an interpreter of the environment 202 that provides a so-called state 204 to the assessment RL agent 200. The state 204 in this context is defined by the set of observations that make up the environment 102, 104, 106. The interpreter 202 may consist of software (a computer program) that assembles the environment 102, 104, 106 into a format that the assessment RL agent 200 can utilize in order to take actions 208. The assessment RL agent's 200 action 208 selection is modeled as a map called a policy. The defined policy may be thought of as a map between the observations made and the actions taken based on these observed observations. The policy map may give the probability of taking a given action when in a given state in some implementations, although non-probabilistic policies may be implemented in some (or all) of the various assessment RL agents 200.

The assessment RL agent 200 is also defined by a state-value function that defines the expected return (or reward 206) when successively following a defined policy. The initial policy and state value function can be defined based on historical assessment outcomes from qualified trained personnel. However, this initial policy and state value function can be updated over time as the assessment RL agent 200 takes further actions 208 and collects additional rewards 206 (e.g., via the reward value function for the assessment RL agent 200) for these actions 208. These rewards 206 may be characterized by soliciting feedback from the treating physician or treating veterinarian as well as soliciting feedback from the patient or pet owner. For example, a survey can be provided that asks whether the assessment (i.e., action 208) provided by the assessment RL agent 200 was correct or not. These surveys may be provided via email and/or may be accessed through an application that has been downloaded to, for example, the user's smart phone or other computing device. These surveys may also be provided via paper, where answers are received and returned via mail, email, facsimile, etc.

In some implementations, it may be desirable to collect feedback via these surveys periodically over time to facilitate implementation and update of the assessment RL agent's 200 longer-term reward functions and policy. For example, feedback may be solicited at the time of treatment as well as a days, weeks, and/or months after treatment. By soliciting feedback over time, the assessment RL agent 200 may be able to fine tune, for example, the actions 208 that the assessment RL agent 200 later takes. By way of non-limiting example, a survey conducted at the time of treatment may provide a given amount of reward 206 to the assessment RL agent 200, while a second survey conducted a month after receiving treatment may provide a second amount of reward 206 (whether negative or positive) to the assessment RL agent 200. In other words, the assessment RL agent 200 may take a given action 208 based on a given set of observations 102, 104 and/or 106 and may receive multiple rewards 206 over time based on the given action 208 taken. These and other variations would be readily apparent to one of ordinary skill given the contents of the present disclosure.

The survey may be implemented by soliciting feedback on a graded scale. This graded scale may include four (4) gradations that range from: (i) assessment was not correct; (ii) don't believe the assessment was correct; (iii) believe the assessment was correct; and (iv) yes, the assessment was correct. While the inclusion of four (4) gradations on the graded scale is exemplary, it would be appreciated by one of ordinary skill given the contents of the present disclosure that more or fewer gradations may be included in alternative implementations. However, utilizing four (4) gradations may prove optimal as lesser degrees of gradation (e.g., two (2)—correct, or not correct) may not provide enough granularity to the reward feedback for the assessment RL agents 200 in order to converge on effective assessments quickly, while more degrees of gradation (e.g., ten (10) levels of gradation) may provide too much subjectivity in the reward feedback loop for the assessment RL agent 200, making it difficult for the assessments determined by the assessment RL agents 200 to converge on desirable solutions. The reward value function 206 may use the survey data in order to update the assessment RL agent's state value function 204.

Figure 3:
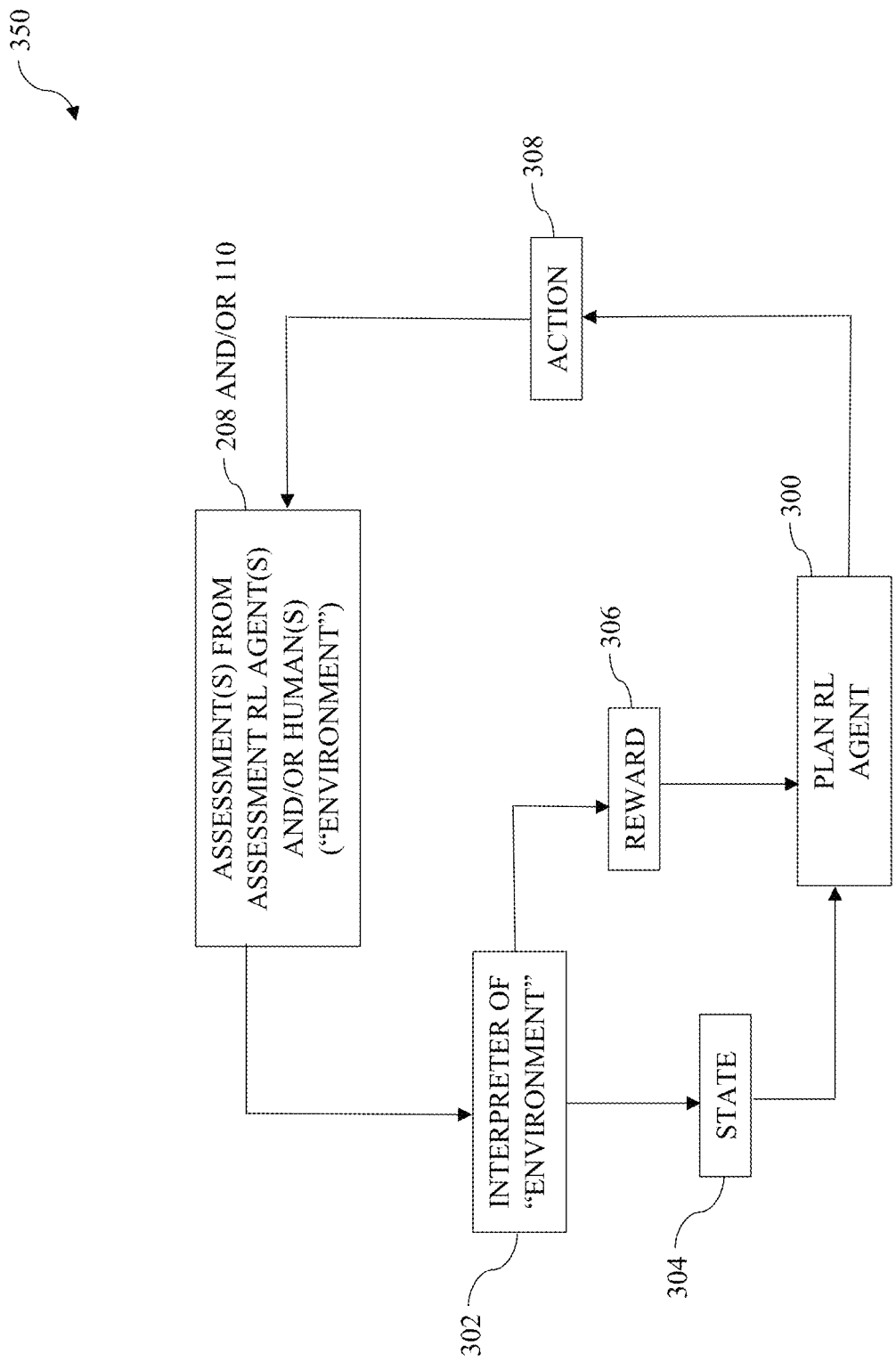
FIG. 3 is a logical block diagram of one exemplary planning reinforcement learning agent, in accordance with the principles of the present disclosure.

Referring now to FIG. 3, an exemplary system 350 implementation of a plan RL agent 300 is shown and described in detail. However, unlike the assessment RL agent's 200 environment 102, 104, 106, the plan RL agent's 300 environment 208 and/or 110 may be the set of assessments provided by the assessment RL agent 200 and/or may be human-based assessments 110. For example, the assessment RL agent 200 may indicate assessment A, assessment B, and assessment X. However, the treating DVM may discard assessment A and only accept assessment B and assessment X. In such a scenario, the plan RL agent's 300 environment 208 and/or 110 may only consist of assessment B and assessment X (or may deprioritize assessment A, while accepting assessment B and assessment X). The goal of the plan RL agent 300 is to take the best action 308 (e.g., to provide the most correct set of diagnostics and treatment recommendations) based on the set of assessments that the assessment RL agent 200 and/or the treating human provides. The assessment RL agent 200 and the plan RL agent 300 are arranged sequentially and are optimized independently from one another. This independent optimization is advantageous as it simplifies the development and optimization of the assessment RL agent's 200 and plan RL agent's 300 respective policies and state value functions. Moreover, incorrect assessments will not negatively affect the optimization of the plan RL agent 300 and vice versa.

Similar to the assessment RL agent 200, the plan RL agent 300 also utilizes an interpreter of the environment 302 that provides a state 304 to the plan RL agent 300. The state 304 in this context is defined by, for example, the set of assessments from the assessment RL agent 200 that make up the environment 208. In some implementations, the "environment" of the plan RL agent 300 may include some portions of the environment 102, 104, 106 of the assessment RL agent 200 (e.g., the objective biological data 106 and/or the tests performed to obtain some (or all) of the objective biological data 106). The interpreter 302 may consist of software (a computer program) that assembles the environment 208 and/or 110 into a format that the plan RL agent 300 can utilize to take actions 308. The initial policy and state value function for the plan RL agent 300 can be defined based on historical diagnostic and treatment recommendations from qualified trained personnel given a particular set of assessments. For example, having acquired knowledge about the environment 208 and/or 110 that is indicative of an obstruction within the animal, the plan agent's 300 policy may be to advise on surgery as the appropriate action 308 to take. Moreover, similar to that discussed supra with respect to the assessment RL agent 200, this initial policy and state value function can be updated over time as the plan RL agent 300 takes further actions 308 and collects rewards 306 for these actions 308.

The actions 308 taken by the plan RL agent 300 may be ranked or otherwise prioritized. For example, a given diagnostic and/or a given treatment plan may be initially given a highest level of confidence over other diagnostic and/or treatment plans given a set of assessments provided by the assessment RL agent 200 and accordingly would be prioritized for display on the treatment/recommendation GUI 108. This may be determined by diagnostic and/or treatment plans that have previously yielded the highest long-term rewards for a given set of assessments. However, another diagnostic test that has yet to be performed may be a strong indicator for the given treatment plan and may also be determined to be a quick and relatively inexpensive diagnostic test. In such an instance, the other diagnostic test may be subsequently prioritized over the given diagnostic and/or given treatment plan previously determined to strengthen (or weaken) the given diagnostic and/or given treatment plan. In some implementations, such a scheme may be implemented through a semi-supervised machine learning scheme, with the results being implemented in the reward value function for the plan RL agent 300 in order to further optimize the performance of the system 100 in future use.

The rewards 306 (e.g., as determined by the reward value function for the plan RL agent 300) may be characterized by soliciting feedback from the treating physician or treating veterinarian as well as soliciting feedback from the patient or pet owner similar to that described for the assessment RL agent 200. For example, a survey can be provided (e.g., via e-mail, in-app, paper, etc.) that asks whether the diagnostic and treatment recommendations (i.e., action 308) provided by the plan RL agent 300 was correct or not on a per-diagnostic or per-treatment recommendation basis. Similar to the assessment RL agent 200 discussion supra, it may be desirable to collect feedback via these surveys periodically over time to facilitate implementation and update of the plan RL agent's 300 longer-term reward functions and policy. For example, feedback may be solicited at the time of treatment as well as a days, weeks, and/or months after treatment. By soliciting feedback over time, the plan RL agent 300 may be able to fine tune, for example, the actions 308 (e.g., treatments and/or additional diagnostics) that the plan RL agent 300 later takes. In other words, the plan RL agent 300 may take a given action 308 based on a given set of assessments 208 and/or 100 and may receive multiple rewards 306 over time based on the given action 308 taken. These and other variations would be readily apparent to one of ordinary skill given the contents of the present disclosure.

This survey may also be implemented by soliciting feedback on a graded scale. For example, this graded scale may include four (4) gradations that range from: (i) the diagnostic and treatment recommendations did not help; (ii) do not believe the diagnostic and treatment recommendations helped; (iii) believe the diagnostic and treatment recommendations helped; and (iv) yes, the diagnostic and treatment recommendations helped. While the inclusion of four (4) gradations on the graded scale is exemplary, it would be appreciated by one of ordinary skill given the contents of the present disclosure that more or fewer gradations may be included in alternative implementations. The reward value function 306 may use the survey data in order to update the plan RL agent's state value function 304.

Exemplary Reinforcement Learning Methodologies—

Figure 4:
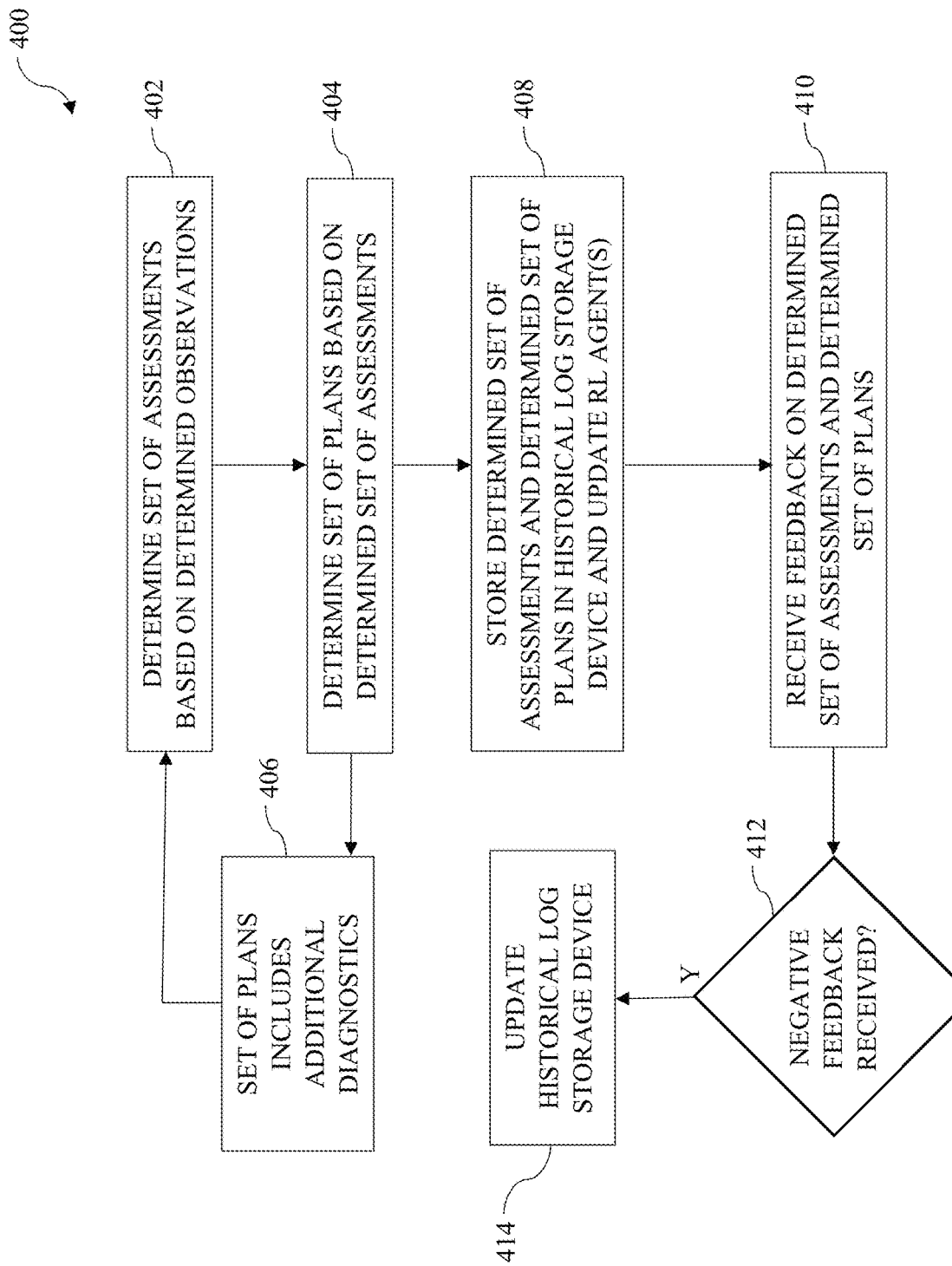
FIG. 4 is a logical flow diagram of one exemplary method for receiving feedback on a determine set of assessments and a determined set of plans, in accordance with the principles of the present disclosure.

Referring now to FIG. 4, one exemplary methodology 400 for the updating of the assessment RL agents' 200 and the plan RL agents' 300 policy over time is shown and described in detail. At operation 402, the assessment RL agent 200 determines a set of assessments based on a set of determined observations. For example, and as described previously herein, these determined observations may include outputs from the classification AI engines 102 as is disclosed in commonly owned U.S. patent application Ser. No. 16/578, 182 filed Sep. 20, 2019 and entitled "Methods and Apparatus for the Application of Machine Learning to Radiographic Images of Animals", now U.S. Pat. No. 10,593,041, the contents of which were previously incorporated herein by reference supra; may include subjective biological data 104; and/or may include objective biological data 106.

At operation 404, the plan RL agent 300 determines a set of plans based on the determined set of assessments by the assessment RL agent 200. As discussed elsewhere herein, the set of plans may include treatment recommendations based on the set of determined assessments. In some implementations, the set of plans may also include further diagnostic testing recommendations for the patient. For example, the assessment RL agent 200 may indicate an assessment with a borderline confidence level associated with it. In other words, the assessment RL agent 200 may indicate a statistically significant assessment; however, the statistically significant assessment may be lower than a predetermined threshold. In such an instance, the set of plans determined by the plan RL agent 300 may include additional diagnostics to be performed at operation 406.

As but another non-limiting example, the plan RL agent 300 may determine that an assessment indicated by the assessment RL agent 200 can be quickly confirmed (or discarded) based on a diagnostic test that was not included with the "environment" assessed by the assessment RL agent 200. Accordingly, the set of plans determined by the plan RL agent 300 may include additional diagnostics to be performed at operation 406. In some implementations, some (or all) of the information provided as part of the environment of the assessment RL agent 200 may be passed along to the plan RL agent 300 in order to aid in the determination of appropriate diagnostic tests to be included with the set of plans determined by the plan RL agent 300 at operation 404. If the set of plans from the plan RL agent 300 includes additional diagnostic tests to be performed, the process may be repeated starting at operation 402 with data from these additional diagnostic tests now being included in the environment of the assessment RL agent 200.

At operation 408, the determined set of assessments obtained at operation 402 and the determined set of plans obtained at operation 404 may be stored in a storage device (e.g., a physical hard drive, data storage in the cloud, or other means of storing data). This stored data in the historical data store may be utilized to update the policies for the assessment RL agent 200 and/or the plan RL agent 300. In some implementations, the historical data store may include, in addition to the determined set of assessments obtained at operation 402 and the determined set of plans obtained at operation 404, a historical log of the observations made, the actions taken 208 and/or 308, as well as the rewards 206 and/or 306 received.

At operation 410, feedback is received on the determined set of assessments determined at operation 402 as well as the determined set of plans determined at operation 404. If negative feedback is received at operation 412, the historical log storage device is updated at operation 414. For example, when an observation for one or more of the assessment RL agent 200 and/or the plan RL agent 300 is disqualified based off the received feedback at operation 410 (i.e., meaning it was an incorrect observation), one or more of the log entries is invalidated and the learning from this experience is reverted. In other words, the plan RL agent 300 may observe a first diagnosis and may take a first action plan based off this observed first diagnosis. The assessment RL agent 200 and/or the plan RL agent 300 may later receive a negative reward (or a reward that is not as high as the assessment RL agent 200 and/or the plan RL agent 300 were expecting to receive), the first diagnosis, the first action plan, and the rewards for the first diagnosis and/or the first action plan may all be invalidated (or removed) from the historical log storage device at operation 414 so that the assessment RL agent 200 and/or the plan RL agent 300 do not learn (or forget) this particular example and do not update their respective policies from this experience.

As but another non-limiting example, the assessment RL agent 200 may determine a set of assessments based off observation A, observation B, and observation C. The assessment RL agent 200 may determine a same set of assessments based off observation A, observation B, and observation X. If the plan RL agent 300 gets positively rewarded for the set of assessments based off observation A, observation B, and observation C, but get negatively rewarded for the same set of assessments based off observation A, observation B, and observation X, the historical log storage device may invalidate (or remove) the data for the latter plan while retaining the data for the former plan. These and other examples would be readily apparent to one of ordinary skill given the contents of the present disclosure.

Exemplary Treatment/Recommendation Graphical User Interfaces—

Referring now to FIGS. 5A-5E, one exemplary series of treatment/recommendation GUIs 108 is shown and described in detail. Specifically, in FIG. 5A a first GUI 108 is shown that includes three (3) patients that include: (i) patient SmokeySmoke 502; (ii) patient Annie 504; and (iii) patient Quasimodo 506. Each of these patients 502, 504, 506 may include a timestamp, a name, a patient identification, as well as a summary of findings. For example, patient SmokeySmoke 502 includes a strong abnormal finding for a vertebral heart score (symbolized as "VHS"). Patient Annie 504 includes a strong abnormal finding for both a mid-abdominal mass (presence of a mass in the ventral mid abdomen, symbolized as "MAM") as well as the presence of fluid in the peritoneal space (symbolized as "PFL"). Patient Annie 504 also includes a weaker abnormal indicating enlargement of the spleen (splenomegaly, symbolized as "SMG"). Patient Quasimodo 506 includes a strong abnormal finding for the presence of moderate to large round soft tissue opacity within the lung tissue of the patient (symbolized as "PMS") as well as a weaker abnormal indicating the presence of an enlarged liver (hepatomegaly, symbolized as "HMG"). In this illustrated example, the user of the GUI has chosen patient 502 as indicated by the highlighted portion 508.

Figure 5A:
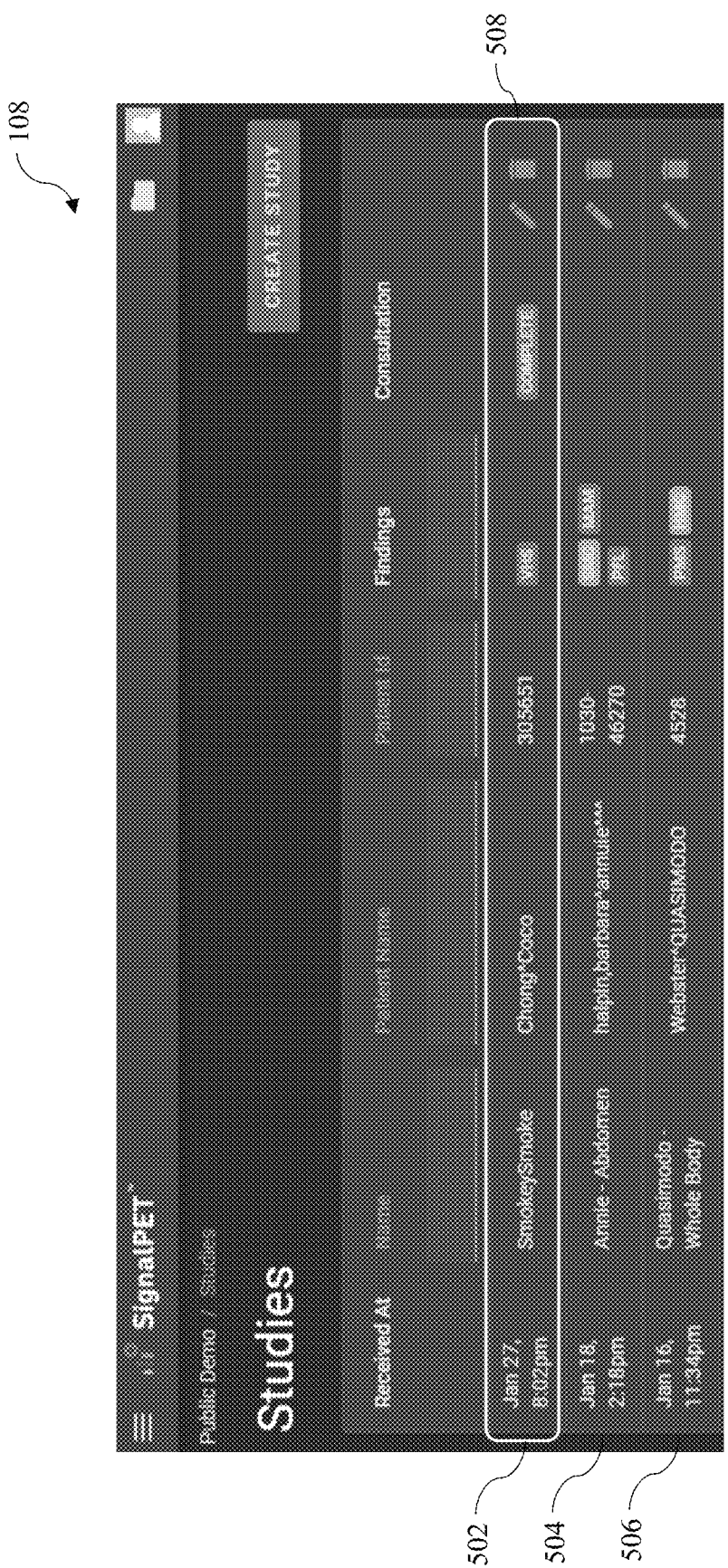
FIG. 5A is a first exemplary graphical user interface display indicative of assessment findings for a plurality of animals, in accordance with the principles of the present disclosure.
Figure 5B:
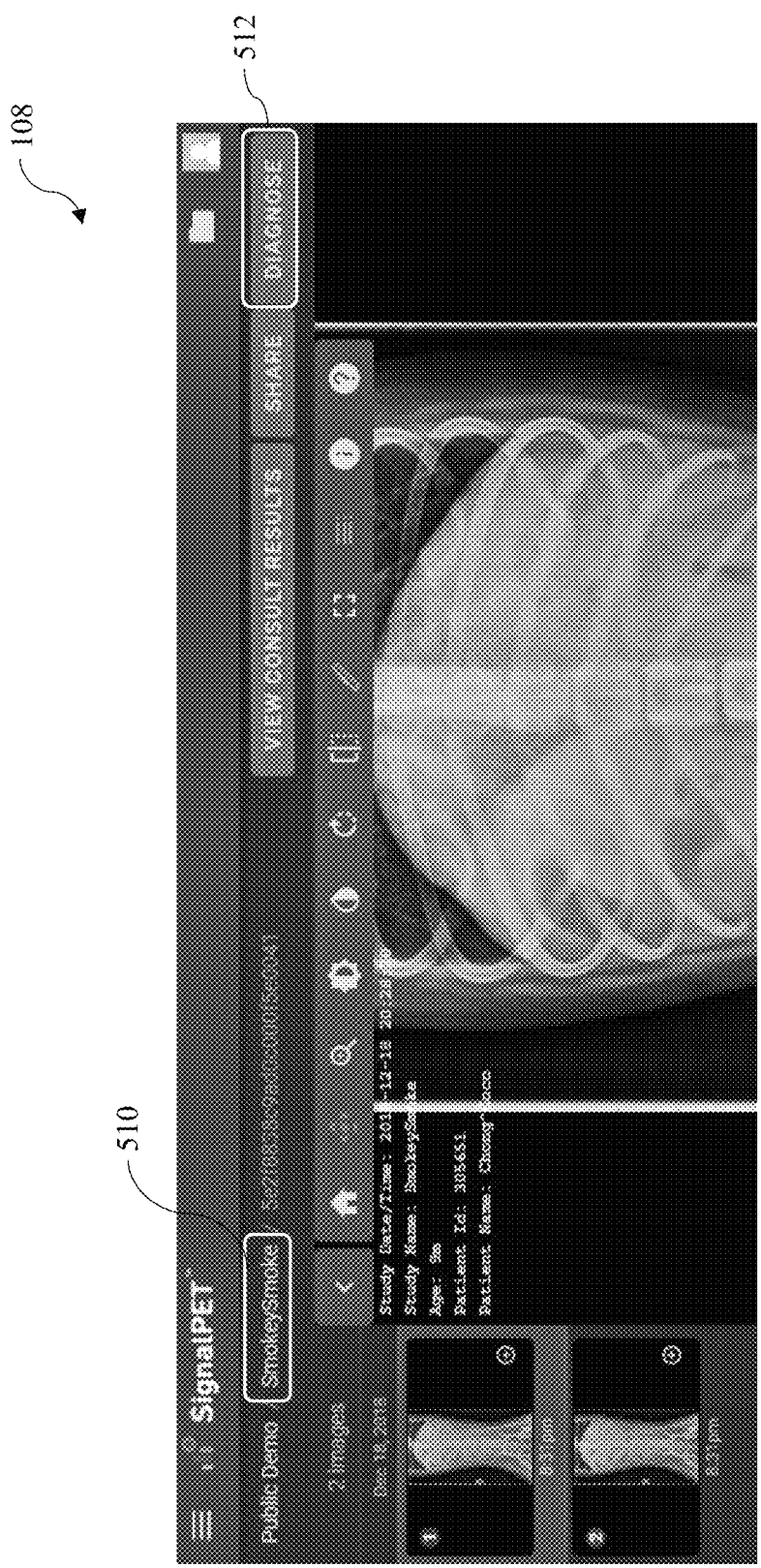
FIG. 5B is a second exemplary graphical user interface display indicative of a radiological image for a given animal, in accordance with the principles of the present disclosure.
Figure 5C:
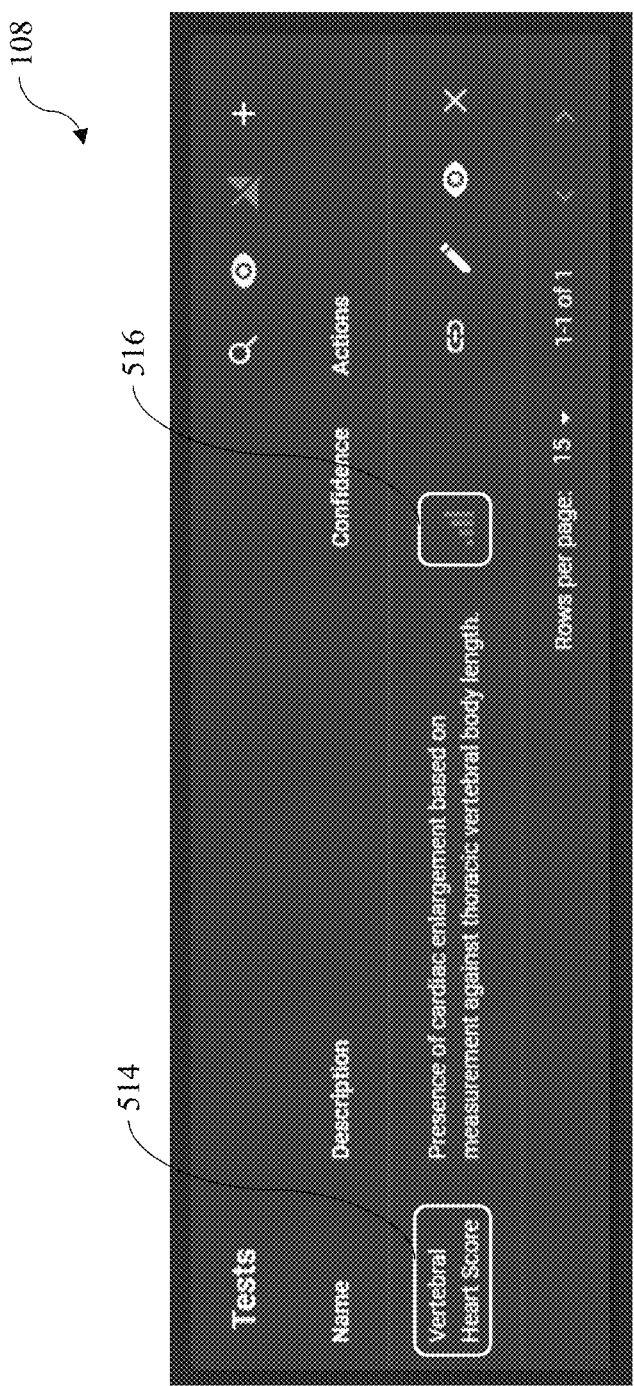
FIG. 5C is a third exemplary graphical user interface display indicative of tests for a given animal, in accordance with the principles of the present disclosure.
Figure 5D:
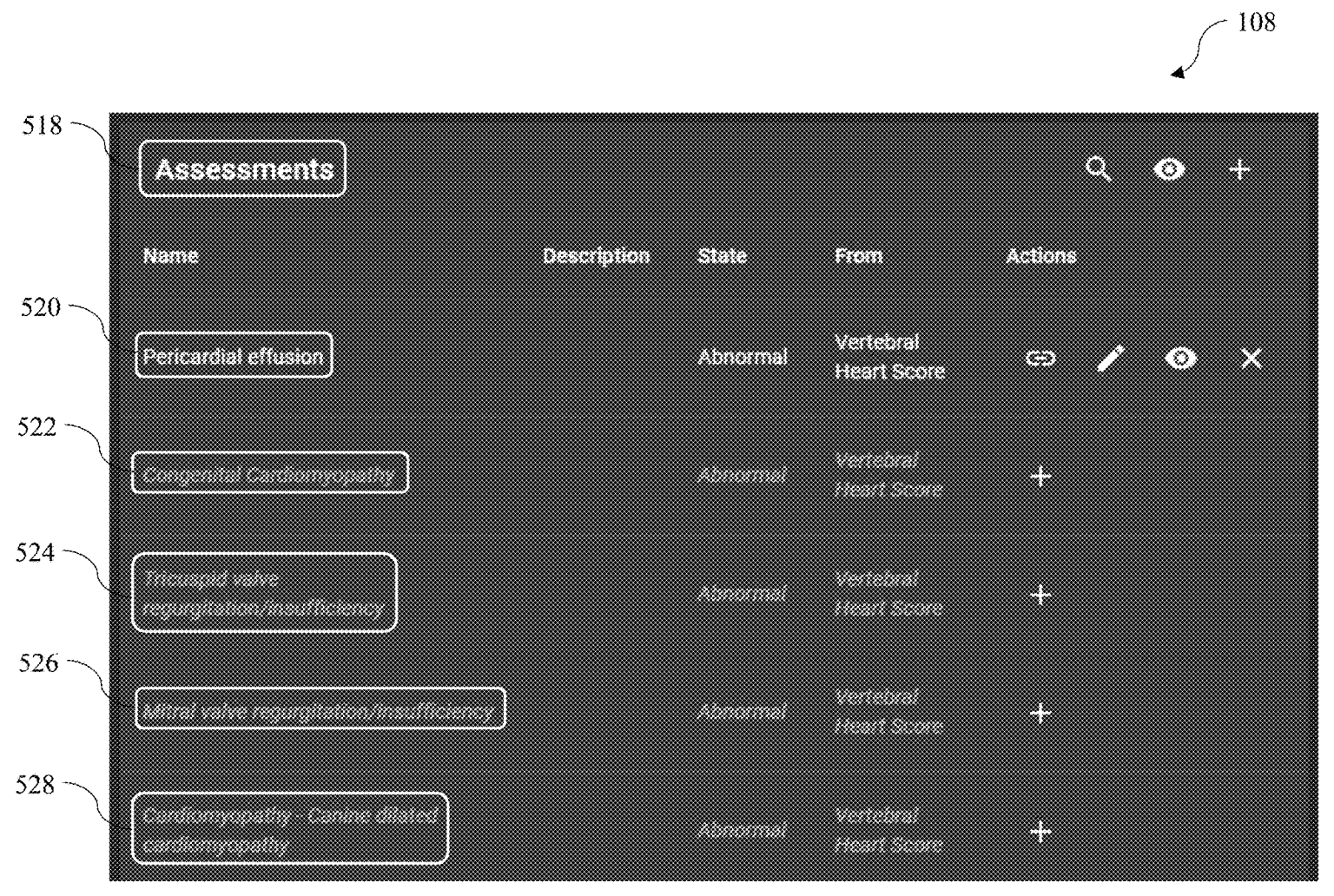

After selection of the chosen patient 502, FIG. 5B presents some radiographic images taken of patient 502. As shown in the GUI 108 of FIG. 5B, the patient's name is illustrated on the page in highlighted portion 510. The GUI 108 includes each of the radiographic images on the left-hand side of the GUI, with the upper most radiographic image being highlighted and also being shown in an enlarged image to the right of the two smaller radiographic images. A user of the GUI 508 may then select "diagnose" 512 in order to view a summary of the findings found by system 100. FIG. 5C illustrates the strongly abnormal vertebral heart score indication 514 as indicated by the confidence level indicator 516 in GUI 108. The strongly abnormal vertebral heart score indication 514 includes a description of the abnormality which indicates the presence of cardiac enlargement based on a measurement against the thoracic vertebral body length.

Using the output of the classification AI engine 102 as is described in co-owned U.S. patent application Ser. No. 16/578,182 filed Sep. 20, 2019 and entitled "Methods and Apparatus for the Application of Machine Learning to Radiographic Images of Animals", now U.S. Pat. No. 10,593,041, the contents of which were previously incorporated herein by reference supra, as well as subjective biological data 104 and objective biological data 106, a set of assessments 518 is given for the strong abnormal vertebral heart score abnormality in the GUI of FIG. 5D. Specifically, the following assessments have been determined by the assessment RL agent 200 of the system, namely: (i) a pericardial effusion assessment 520; (ii) a congenital cardiomyopathy assessment 522; (iii) a tricuspid valve regurgitation/insufficiency assessment 524; (iv) a mitral valve regurgitation/insufficiency assessment 526; and (v) a cardiomyopathy assessment 528.

Figure 5E:
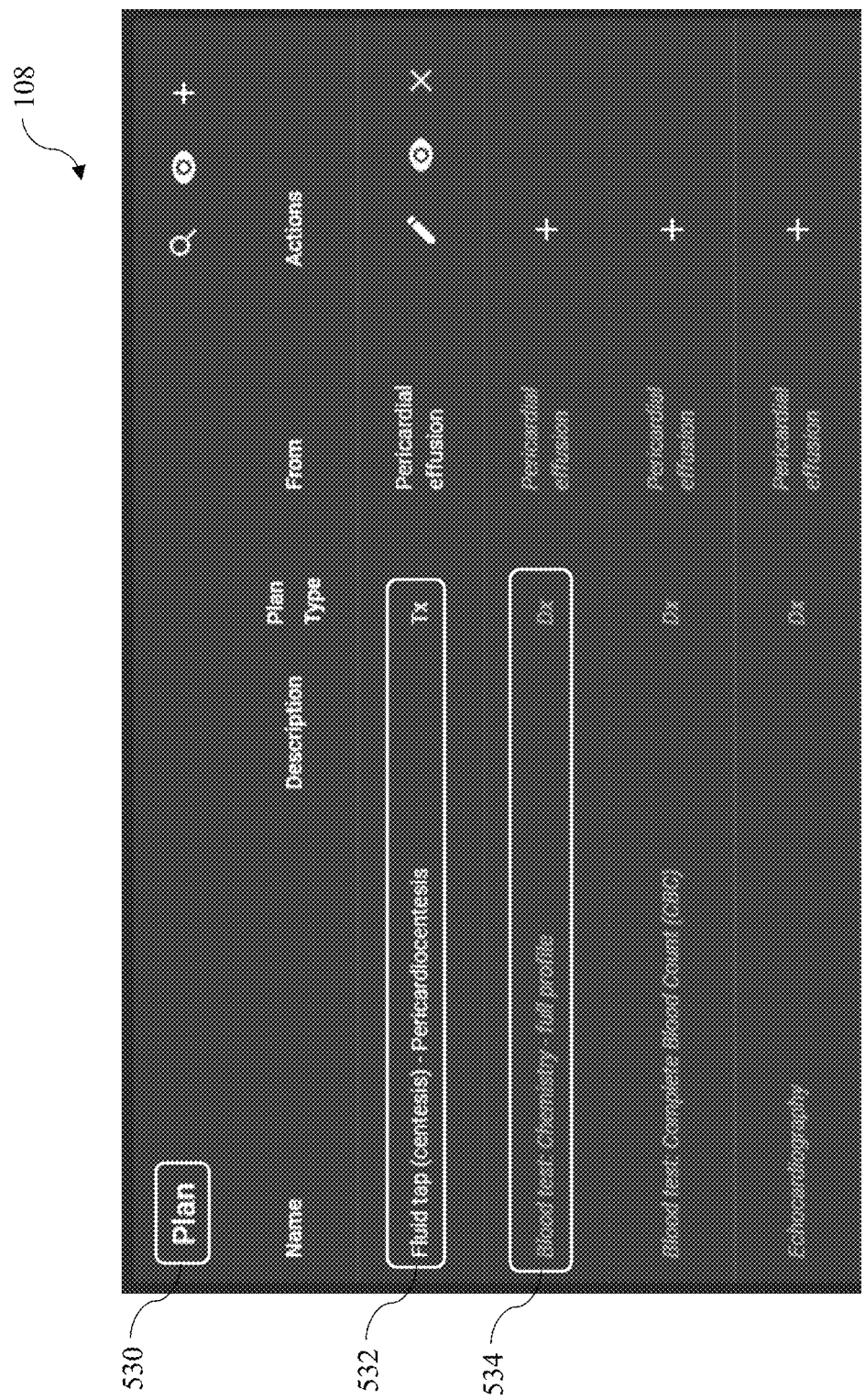
FIG. 5E is a fifth exemplary graphical user interface display indicative of a set of treatment plans and additional diagnostic test suggestions for a given animal, in accordance with the principles of the present disclosure.

In FIG. 5E, a set of treatment and diagnostic plans 530 have been indicated by the plan RL agent 300 as shown in the GUI 108. Specifically, a treatment plan 532 is indicated by the plan type "Tx" which suggests a fluid tap (centesis)—pericardiocentesis as a treatment plan for the assessed pericardial effusion condition. Additionally, a diagnostic recommendation 534 is also indicated by the plan type "Dx", which suggests a full profile chemistry blood test for the assessed pericardial effusion condition. While FIGS. 5A-5E illustrates a specific series of GUI 108 displays, it would be readily appreciated that the specific tests, assessments, and plans made by the system 100 would be dependent upon the actual condition for a given animal patient.

Figure 6A:
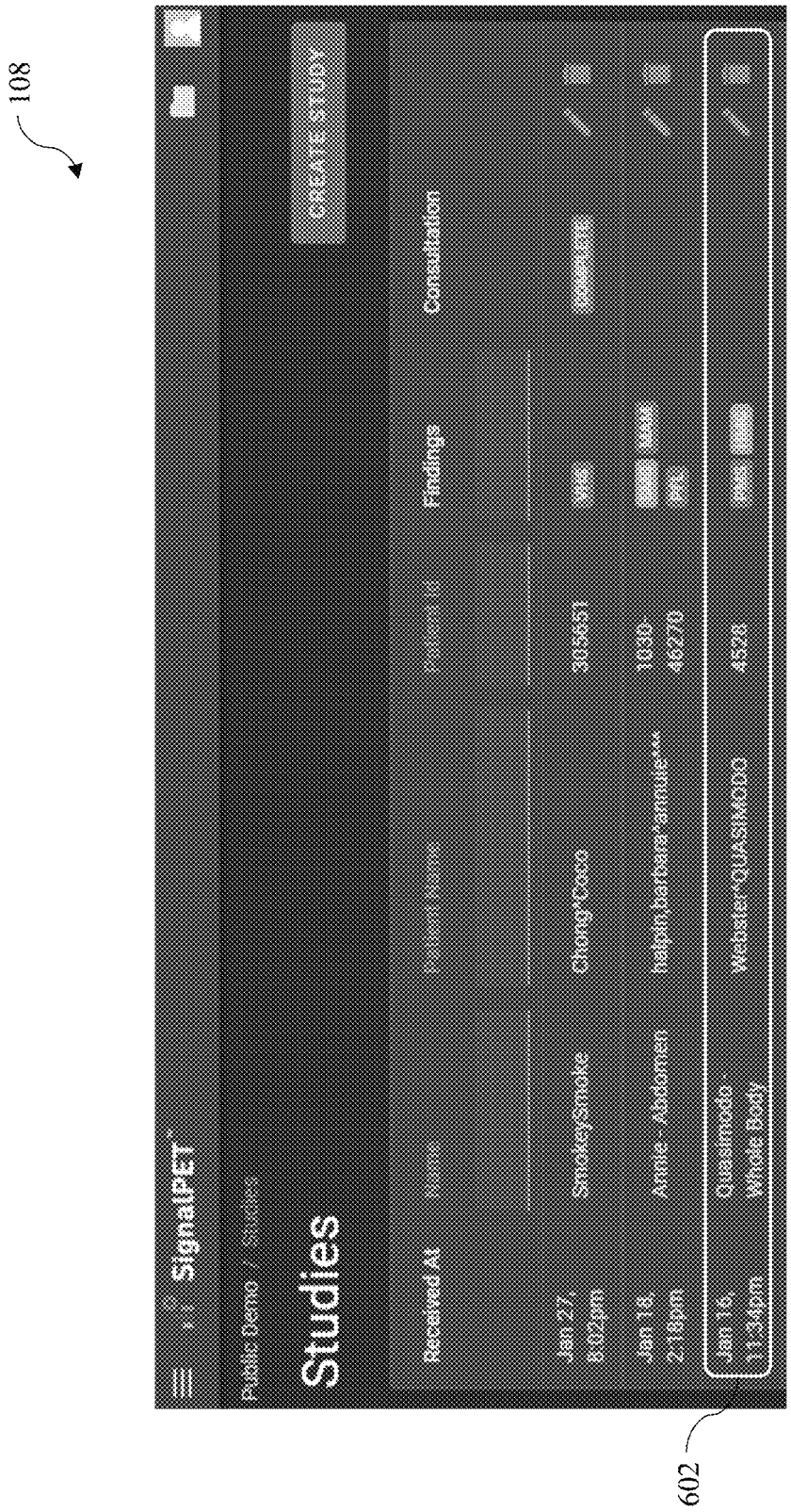
FIG. 6A is the first exemplary graphical user interface display indicative of assessment findings for a plurality of animals of FIG. 5A, in accordance with the principles of the present disclosure.
Figure 6B:
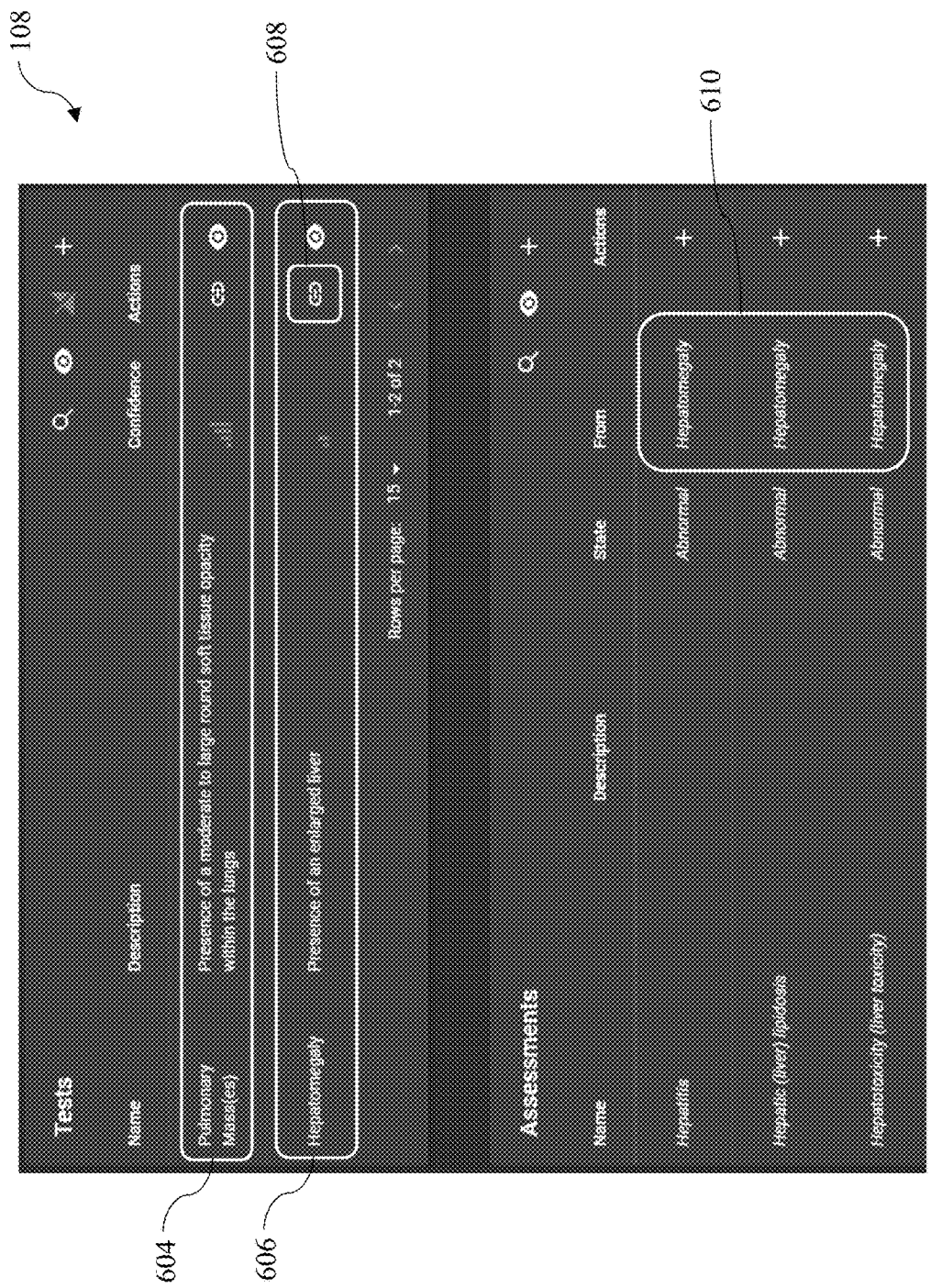
FIG. 6B is a sixth exemplary graphical user interface display indicative of multiple tests and a set of assessment findings for a given animal, in accordance with the principles of the present disclosure.
Figure 6C:
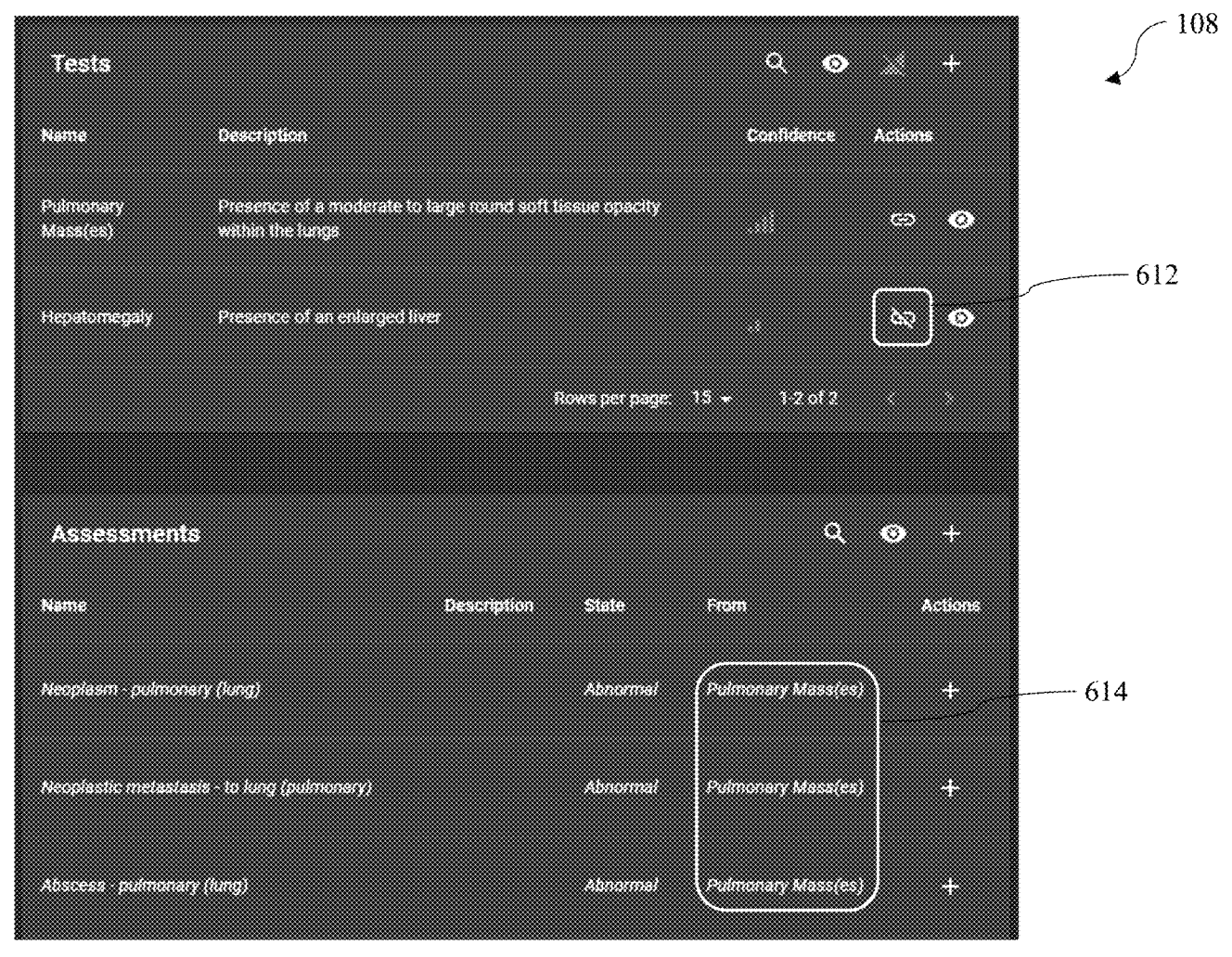

FIGS. 6A-6C illustrate one such alternative series of GUIs 108. Specifically, as shown in FIG. 6A, the user of the GUI 108 selects patient Quasimodo 602. Upon selection of Quasimodo 602, the user is displayed the GUI 108 of FIG. 6B which indicates a strong abnormality for the presence of a moderate to large round soft tissue opacity with the lungs as indicated by selection 604, as well as a weaker abnormality for the presence of an enlarged liver as indicated by selection 606. The assessments made by assessment RL agent 200 may indicate an assessment of hepatitis, hepatic (liver) lipidosis, and hepatotoxicity, all of which relate to the hepatomegaly test 610 as indicated by the output of the classification AI engines 102, subjective biological data 104, and/or objective biological data 106. The user of the GUI 108 may decide that the presence of hepatomegaly 606 is not of major concern and may deselect this test by selecting the action button 608 on the GUI.

FIG. 6C illustrates an alternative set of assessments being made with the hepatomegaly test being de-selected as indicated by icon 612. As shown in the assessments portion of the GUI 108, the assessments are now all related from the data associated with the presence of pulmonary mass(es) 614, namely, the presence of a neoplasm in the lungs, the presence of neoplastic metastasis in the lungs, as well as an abscess in the lung. Given this de-selection of the hepatomegaly test and assessments, a plan may now be constructed for the treatment of the patient Quasimodo as well as further diagnostic tests for the patient with the user of the GUI 108 having deselected the presence of an enlarged liver (hepatomegaly) from the set of tests and assessments. Again, while FIGS. 6A-6C illustrates a specific series of GUI 108 displays, it would be readily appreciated that the specific tests, assessments, and plans made by the system 100 would be dependent upon the condition for a given animal patient.

It will be recognized that while certain aspects of the present disclosure are described in terms of specific design examples, these descriptions are only illustrative of the broader methods of the disclosure and may be modified as required by the particular design. Certain steps may be rendered unnecessary or optional under certain circumstances. Additionally, certain steps or functionality may be added to the disclosed embodiments, or the order of performance of two or more steps permuted. All such variations are considered to be encompassed within the present disclosure described and claimed herein.

While the above detailed description has shown, described, and pointed out novel features of the present disclosure as applied to various embodiments, it will be understood that various omissions, substitutions, and changes in the form and details of the device or process illustrated may be made by those skilled in the art without departing from the principles of the present disclosure. The foregoing description is of the best mode presently contemplated of carrying out the present disclosure. This description is in no way meant to be limiting, but rather should be taken as illustrative of the general principles of the present disclosure. The scope of the present disclosure should be determined with reference to the claims.

What is claimed is:

1. A non-transitory computer-readable storage apparatus comprising a plurality of instructions, that when executed by a processor apparatus, are configured to:
   establish a policy and state value function for an assessment reinforcement learning (RL) agent using historical diagnostic assessment outcomes as an input for the establishment of the policy and the state value function for the assessment RL agent;
   establish a policy and state value function for a plan reinforcement learning (RL) agent using historical diagnostic and treatment recommendations for a predetermined set of diagnostic assessments as an input for the establishment of the policy and the state value function for the plan RL agent;
receive a set of observations related to treatment of an animal;
determine a set of diagnostic assessments, using the policy and the state value function for the assessment RL agent, by iteratively training the assessment RL agent using the received set of observations;
determine a set of treatment plans based on the determined set of diagnostic assessments using the policy and the state value function for the plan RL agent;
store the determined set of diagnostic assessments and the determined set of treatment plans in a historical log storage device;
receive feedback on the determined set of diagnostic assessments and using this received feedback on the determined set of diagnostic assessments to update the policy and the state value function for the assessment RL agent; and
receive feedback on the determined set of treatment plans and using this received feedback on the determined set of treatment plans to update the policy and the state value function for the plan RL agent independent from the update of the policy and the state value function for the assessment RL agent;
wherein the independent update of the policy and the state value function for the assessment RL agent from the update of the policy and the state value function for the plan RL agent prevents an incorrect diagnostic assessment determined from the assessment RL agent from negatively affecting optimization of the plan RL agent via invalidation or removal of the incorrect diagnostic assessment stored in the historical log storage device.

2. The non-transitory computer-readable storage apparatus of claim 1, wherein the plurality of instructions, that when executed by the processor apparatus, are further configured to:
output one or more additional set of diagnostic tests to be performed as part of the determined set of treatment plans;
receive results from the one or more additional set of diagnostic tests;
input the results from the one or more additional set of diagnostic tests into the assessment RL agent;
determine an updated set of diagnostic assessments using the assessment RL agent based on the results from the one or more additional set of diagnostic tests; and
generate an updated set of treatment plans based on the determined updated set of diagnostic assessments.

3. The non-transitory computer-readable storage apparatus of claim 1, wherein the plurality of instructions, that when executed by the processor apparatus, are further configured to:
receive feedback on the determined set of diagnostic assessments or the determined set of treatment plans that is negative; and
remove the respective stored set of diagnostic assessments or the stored set of treatment plans from the historical log storage device.

4. The non-transitory computer-readable storage apparatus of claim 1, wherein the plurality of instructions, that when executed by the processor apparatus, are further configured to:
use contents of the historical log storage device to update the policy or reward value function for either or both of the assessment RL agent and the plan RL agent.

5. The non-transitory computer-readable storage apparatus of claim 1, wherein the received set of observations related to the treatment of the animal comprises receipt of one or more of outputs from: one or more classification artificial intelligence engines, an objective biological data storage device, and a subjective biological data storage device.

6. The non-transitory computer-readable storage apparatus of claim 5, wherein the plurality of instructions, that when executed by the processor apparatus, are further configured to:
use one or more human-based diagnostic assessments as input to the plan RL agent to determine the set of treatment plans using the plan RL agent.

7. A method for the application of reinforcement learning (RL) to the treatment of animals, the method comprising:
establishing a policy and state value function for an assessment RL agent using historical diagnostic assessment outcomes as an input for the establishing of the policy and the state value function for the assessment RL agent;
establishing a policy and state value function for a plan RL agent using historical diagnostic and treatment recommendations for a predetermined set of diagnostic assessments as an input for the establishing of the policy and the state value function for the plan RL agent;
determining a set of diagnostic assessments, using the policy and the state value function for the assessment RL agent, by iteratively training the assessment RL agent using a set of observations of an animal;
determining a set of treatment plans based on the determined set of diagnostic assessments using the policy and the state value function for the plan RL agent;
storing the determined set of diagnostic assessments and the determined set of treatment plans in a historical log storage device;
receiving feedback on the determined set of diagnostic assessments and using the received feedback on the determined set of diagnostic assessments to update the policy and the state value function for the assessment RL agent; and
receiving feedback on the determined set of treatment plans and using the received feedback on the determined set of treatment plans to update the policy and the state value function for the plan RL agent independent from the update of the policy and the state value function for the assessment RL agent;
wherein the independent update of the policy and the state value function for the assessment RL agent from the update of the policy and the state value function for the plan RL agent prevents an incorrect diagnostic assessment determined from the assessment RL agent from negatively affecting optimization of the plan RL agent via invalidation or removal of the incorrect diagnostic assessment stored in the historical log storage device.

8. The method of claim 7, wherein the determined set of treatment plans includes one or more additional set of diagnostic tests to be performed;
receiving results from the one or more additional set of diagnostic tests;
inputting the results from the one or more additional set of diagnostic tests into the assessment RL agent;
determining an updated set of diagnostic assessments using the assessment RL agent based on the results from the one or more additional set of diagnostic tests; and generating an updated set of treatment plans based on the determined updated set of diagnostic assessments.

9. The method of claim 7, wherein when the received feedback on the determined set of diagnostic assessments or the determined set of treatment plans is negative, removing the respective stored set of diagnostic assessments or the stored set of treatment plans from the historical log storage device.

10. The method of claim 7, further comprising using contents of the historical log storage device to update the policy or reward value function for either or both of the assessment RL agent and the plan RL agent.

11. The method of claim 7, further comprising receiving one or more of outputs from: one or more classification artificial intelligence engines, an objective biological data storage device, and a subjective biological data storage device, in order to determine the set of observations of the animal.

12. The method of claim 11, further comprising using one or more human-based diagnostic assessments as input to the plan RL agent to determine the set of treatment plans using the plan RL agent.

13. A system configured to apply reinforcement learning (RL) to treatment of animals, the system comprising:
a classification artificial engine that takes as input radiographic images, and outputs classifications for various conditions of an animal;
a subjective biological data storage device that stores subjective biological data for the animal;
an objective biological data storage device that stores objective biological data for the animal;
an assessment RL agent which takes as input the classifications for the various conditions of the animal from the classification artificial engine, the subjective biological data for the animal from the subjective biological data storage device, and the objective biological data for the animal from the objective biological data storage device, and outputs a determined set of diagnostic assessments for the animal based on the inputs using a policy and a state value function for the assessment RL agent by iteratively training the assessment RL agent using the various conditions of the animal from the classification artificial engine, the subjective biological data for the animal from the subjective biological data storage device, and the objective biological data for the animal from the objective biological data storage device;
a plan RL agent which takes as input the determined set of diagnostic assessments for the animal from the assessment RL agent, and outputs a determined set of treatment plans for the treatment of the animal based on the determined set of diagnostic assessments from the assessment RL agent using a policy and a state value function for the plan RL agent;
a historical log storage device which stores the determined set of diagnostic assessments and the determined set of treatment plans;

wherein the system:
establishes the policy and the state value function for the assessment RL agent using historical assessment outcomes as an input for the establishment of the policy and the state value function for the assessment RL agent;
establishes the policy and the state value function for the plan RL agent using historical diagnostic and treatment recommendations for a predetermined set of diagnostic assessments as an input for the establishment of the policy and the state value function for the plan RL agent;
receives feedback on the determined set of diagnostic assessments and using this received feedback on the determined set of diagnostic assessments to update the policy and the state value function for the assessment RL agent; and
receives feedback on the determined set of treatment plans and using this received feedback on the determined set of treatment plans to update the policy and the state value function for the plan RL agent independent from the update of the policy and state value function for the assessment RL agent;
wherein the independent update of the policy and the state value function for the assessment RL agent from the update of the policy and the state value function for the plan RL agent prevents an incorrect diagnostic assessment determined from the assessment RL agent from negatively affecting optimization of the plan RL agent via invalidation or removal of the incorrect diagnostic assessment stored in the historical log storage device.

14. The system of claim 13, wherein the determined set of treatment plans includes one or more additional set of diagnostic tests to be performed;
wherein the assessment RL agent receives as input results from the one or more additional set of diagnostic tests in order to generate an updated set of diagnostic assessments; and
wherein the plan RL agent receives as input the updated set of diagnostic assessments and in response thereto, generates an updated set of treatment plans for the treatment of the animal.

15. The system of claim 13, wherein the plan RL agent further takes as input one or more human-based diagnostic assessments, the one or more human-based diagnostic assessments and the determined set of diagnostic assessments from the assessment RL agent being utilized for the determined set of treatment plans generated by the plan RL agent.

16. The system of claim 13, wherein a portion of the contents of the historical log storage device is selectively removed based on the update to a reward value function for either or both of the assessment RL agent and the plan RL agent.

* * * * *